United States Patent
Ross et al.

(10) Patent No.: US 7,530,962 B2
(45) Date of Patent: May 12, 2009

(54) METHOD FOR DETECTING THE DISCONNECTION OF AN EXTRACORPOREAL DEVICE USING A PATIENT'S ENDOGENOUS ELECTRICAL VOLTAGES

(76) Inventors: Edward Allan Ross, 8917 SW. 42nd Pl., Gainesville, FL (US) 32608; Rosalind J. Sadleir, 1020 NE. 3rd St., Gainesville, FL (US) 32601

( * ) Notice: Subject to any disclaimer, the term of this patent is extended or adjusted under 35 U.S.C. 154(b) by 263 days.

(21) Appl. No.: 11/422,891

(22) Filed: Jun. 8, 2006

(65) Prior Publication Data
US 2007/0000847 A1    Jan. 4, 2007

Related U.S. Application Data

(60) Provisional application No. 60/690,840, filed on Jun. 16, 2005.

(51) Int. Cl.
*A61M 37/00* (2006.01)
*C02F 1/00* (2006.01)
*G01F 1/86* (2006.01)

(52) U.S. Cl. .................. 604/4.01; 604/6.06; 210/739; 210/741; 73/861.02

(58) Field of Classification Search .................. 422/44; 604/4.01, 5.01, 5.04, 6.06, 6.09, 6.01; 210/645, 210/646, 739, 746, 634; 73/861.02; 600/371, 600/373, 381
See application file for complete search history.

(56) References Cited

U.S. PATENT DOCUMENTS

| | | |
|---|---|---|
| 6,736,789 B1 | 5/2004 | Spickermann |
| 6,979,306 B2 | 12/2005 | Moll |
| 2003/0195454 A1 | 10/2003 | Warriar et al. |
| 2004/0254513 A1 | 12/2004 | Shang et al. |
| 2005/0010157 A1 | 1/2005 | Baraldi et al. |
| 2005/0049323 A1 | 3/2005 | Gvozdic |

*Primary Examiner*—Leslie R Deak
(74) *Attorney, Agent, or Firm*—Christine Q. McLeod; Beusse, Wolter, Sanks, Mora & Maire, P.A.

(57) ABSTRACT

The present invention describes a system, apparatus, and method for detection of disconnection of a device from a patient, such as dislodgment of a device during medical treatments or therapies, using a patient's electrical voltages.

18 Claims, 5 Drawing Sheets

METHOD FOR DETECTING THE DISCONNECTION OF AN EXTRACORPOREAL DEVICE USING A PATIENT'S ENDOGENOUS ELECTRICAL VOLTAGES

CROSS-REFERENCE TO RELATED APPLICATIONS

This application claims benefit of U.S. provisional patent application No. 60/690,840, filed Jun. 16, 2005, incorporated herein by reference.

FIELD OF INVENTION

The present invention relates generally to systems and methods for detection of disconnection of a device from a patient. More specifically, the present invention relates to systems and methods for detection of disconnection of a device from a patient, such as dislodgment of a device during medical treatments or therapies, using a patient's electrical voltages.

BACKGROUND OF INVENTION

Many extracorporeal therapeutic procedures have in common the need to remove blood from the body and then return it after processing. These therapies include intermittent treatments (e.g. daily or thrice weekly) such as hemodialysis, hemofiltration, and hemapheresis, as well as a variety of similar but continuous procedures (such as continuous venovenous hemodialysis, hemofiltration and combinations thereof, and extracorporeal membrane oxygenation).

Accidental disconnection of these devices can lead to blood loss, especially at the high flow states typical for mechanically pumped renal replacement therapies. At blood flows of over 400 ml/min, undetected disconnection of returning blood could thus lead to multiple liters of hemorrhage in just a few minutes. This would cause profound illness, with the hemodynamic consequences of low blood pressure, reduced oxygen delivery to the vital tissues, risk of needing blood transfusion, and could result in myocardial infarction, stroke or even death.

Unfortunately, the prior methodology to detect disconnections is not ideal, and tragic complications still occur. The rate of blood loss is so high that it can be severe before medical staff might notice the hemorrhage, and often the patients are so ill that they might not feel or be able to communicate the catastrophic circumstance.

The prior art has addressed this potentially fatal extracorporeal complication by a variety of pressure and air-detector sensors that monitor the blood tubing. The success or lack of success from these approaches depends on whether the tubing disconnection occurs at the tubing segment carrying blood away from the patient (known as the "arterial" tubing) as opposed to the portion returning the processed blood to the body (the "venous" tubing). In the former circumstance, the arterial disconnection disrupts the flow of blood to the pump, which is detectable by virtue of air being pulled into the system or by a change in the relatively high pressure profile within the tubing. Thus, various rapid alarm states typically alert the medical staff to remedy hemorrhage from the disconnection, hopefully before significant quantities of blood are lost. While imperfect, those arterial disconnection detection methods are far more effective than those that attempt to sense venous disconnections. Those scenarios continue to be fraught with great risk of harm, despite safeguards that are universally required and built into the therapeutic medical devices.

The difficulty in detecting disconnections of that portion of the extracorporeal device and/or tubing that returns blood to the patient arises from the conceptual basis of the current technology. All commercial devices sense disconnections based on the pressure profile of the returning blood. Typically the tubing's intraluminal pressure is mechanically and continuously measured by use of a transducer connected to the blood's flow path (e.g. the tubing or specialized cuvettes). Disconnection would be sensed by a fall in the intraluminal tubing pressure of the blood being returned to the patient. Unfortunately, this approach is problematic, and thus not ideal, due to the pressure profiles inherent to extracorporeal therapies: The preferred embodiment of those medical devices is to have the returning pumped (venous) blood be in a low-pressure system. In fact, the pressure within the vein to which the treated blood returns is ideally much less than 50 mm Hg, often less 15 mm Hg. This low range of pressure within the patient's vasculature (effectively resisting the return of the blood to the body's vein) is often much less than the high pressure state within the long tubing carrying the pumped blood. Use of a needle (or catheter) at the end of the tubing in order to gain entry to the vein adds additional resistance, further raising the "venous" pressure profile to levels typically over 100 mg Hg and as high as 300 mm Hg. Thus, the pressure contributed by the patient's vein may be a small fraction of the total pressure within the return side of the extracorporeal tubing. Should the venous needle fall out, or be disconnected for example, the resultant drop in pressure can be such a small percent of the total pressure that it is undetected by the alarm circuitry.

The industry has responded to this problem by making the pressure monitor more sensitive to decreases in pressure; however, current methodologies are by necessity a compromise. Too great a sensitivity leads to false alarms as there are often mild fluctuations in pressure in the venous tubing such as those due to bends or kinks in the tubing, changing positions in the patient or patient's extremities. Too low a sensitivity avoids false alarms but allows more disconnections to be undetected. Furthermore, as medical advances lead to improvements in access to the body's vasculature (e.g. better arteriovenous fistulas or grafts), there will be even less resistance afforded by those structures: thus, an even smaller pressure drop would need to be detected by the conceptually unsatisfactory pressure-drop methodology.

The prior art also includes many inventions and devices that monitor a patient's electrical bioimpedance. Those methods share the feature that an electrical current is applied from an external generator, and pass through the patient using a variety of configurations of transmitting and sensing electrodes. Many such devices are marketed for the purposes of detecting changes in body composition, by virtue of altered impedance. Indeed, some such devices are sold for extracorporeal therapies as a means of guiding the medical prescription, and changes in impedance are used as an index of water and solute removal. None of those prior patented and marketed devices were designed to detect loss of the continuity of the externally generated current (or the resultant change in impedance) as a means of sensing a disconnection.

U.S. Patent Application No. US 2003/0195454 to R. Wariar, J. Han, G. Lamberson, T.P. Hartranft and T. Falkvall describes a new embodiment of bioimpedance technology to detect an extracorporeal device disconnection. In their preferred embodiment, they use an external current generator to establish an electrical circuit via the arterial and venous limbs of the tubing; changes in impedance would be interpreted as a disconnection, triggering an appropriate alarm condition.

However, the older bioimpedance technology as well as the more recent variation proposed by Wariar et al. (US 2003/0195454) are seriously flawed for routine use in patients, in that all those approaches by necessity apply an external current to (and through) the blood and body. The two major detriments to the external current generator approach are: 1) the safety concerns from any external power supply, or malfunctions thereof, directly energizing the extracorporeal blood; and 2) the possible detrimental effects of electrical currents on therapeutic electrical devices implanted in the patient (e.g. life sustaining pacemakers, automated implanted defibrillators) or used to monitor critically ill patients (e.g. intensive care unit hemodynamic monitors, external pacemakers, ventilators). Indeed the topic of even trivial electrical leaks from medical apparatuses into patients has been of grave concern in the literature and manufacturing industry.

The following patents are incorporated herein by reference: U.S. Patent Application No. 2003/0195454 and U.S. Pat. No. 6,979,306.

Accordingly since significant morbidity or mortality can result from hemorrhage when extracorporeal therapeutic devices incorporating blood pumps are accidentally disconnected from patients, there is a need in the art for adequate detection devices. Unfortunately, the current art is inadequate. Accordingly, there is a need in the art for systems and methods for detection of disconnection of a device, such as dislodgment of a device during medical treatments or therapies that do not rely on pressure or apply external currents.

SUMMARY OF THE INVENTION

The present invention is designed to address this need. Specifically, the invention overcomes existing methodology problems by detecting disconnection by utilizing circuitry that passively monitors electrical voltages produced by the patient's body (henceforth called the patient's endogenous electrical voltages). These endogenous voltages are produced by a variety of tissues, primarily the heart and other muscles, and are in contradistinction to exogenously applied currents (such as those from external current generators).

Broadly speaking, the present invention provides a method and system for detecting disconnections based on alterations in the patient's own (endogenous) electrical voltages transmitted via the blood tubing (or alternative conductive pathways) to alarm circuitry. As used herein blood tubing may carry not only blood, but also blood components, or other fluids as known in the art.

Since the sites of blood exiting and returning to the patient are ideally in close proximity, the endogenous electrical signals transmitted via the blood, conductive tubing, or other conductive structures will be nearly identical. In the simplest preferred embodiment of the invention, the presence of connection or disconnection is determined by examining the difference between endogenous voltages at the two points in the extracorporeal blood tubing pathway (leading from and returning to the patient).

Other embodiments of the invention address elements of the extracorporeal therapeutic device in the blood flow path that, depending on their impedance, could alter and thereby confound comparisons of the electrical signals. Those difficulties are overcome by the invention by such embodiments as the use of low impedance blood tubing or roller occlusion blood pumps that increase the impedance of blood flowing through the therapeutic device.

Still other embodiments of the invention use signal processing to discern other patterns of differences between the endogenous electrical signals detected via the blood, blood tubing, or similar structures in the flow path; these include detection of cardiac cycle electrical signals as an indicator of a safe tubing connection, whilst also providing information as to the cardiac rate and rhythm. The various embodiments of the invention incorporate appropriate threshold and noise-eliminating circuitry, as well as robust alarms and technology to alert the medical staff and terminate unsafe blood pumping by the therapeutic device.

In the preferred embodiment, when safely connected to a patient the electrical signals transmitted via the tubing from the two adjacent vascular access sites (one for blood egress and one for return) are nearly identical, and the difference between these two signals (e.g. zero) is monitored and compared by an instrumentation amplifier. Disconnection of one or more sensors causes a greater dissimilarity between the signals and triggers an alarm condition. The configuration and location of the two detector sensors is such that there is low impedance between them whilst in the safe connected status; the signal processing is thereby not confounded by the higher impedance characteristics of the extracorporeal blood flowing henceforth via the tubing through rotating roller occlusion blood pumps or the therapeutic device itself and back to the patient. Appropriately modifying the tubing connected to the patient (so as allow electrical conductance within the blood and/or through the tubing wall) allows the sensors and alarm circuit to be located remote from the patient, such as built into the extracorporeal therapeutic device.

Accordingly, it is an object of the present invention to provide a method for passively monitoring a patient's endogenous electrical voltages so as to detect disconnection of an extracorporeal blood-based therapeutic device and trigger an alarm condition.

It is a further object to provide a method for passively monitoring a patient's endogenous electrical voltages by conductance through blood in tubing, which connects the patient to the extracorporeal blood-based therapeutic device.

It is a further object to provide a method for passively monitoring a patient's endogenous electrical voltages by use of the tubing, which connects the patient to the extracorporeal blood-based therapeutic device, with the tubing being fabricated so as to incorporate a conductive moiety.

It is a further object to provide a method for passively monitoring a patient's endogenous electrical voltages by use of conductive wires connected to the patient.

It is a further object to provide a method for detecting disconnection of an extracorporeal blood-based therapeutic device by comparison of the endogenous electrical signals detected at sensors incorporated into (or attached to) tubing carrying blood leaving and returning to a patient.

It is a further object to provide a method for detecting disconnection of an extracorporeal blood-based therapeutic device by comparison of the endogenous electrical signals detected at sensors incorporated into (or attached to) tubing carrying blood leaving and returning to a patient, in which similarity of the signals is indicative of safe connection and dissimilarity is indicative of disconnection.

It is a further object to provide a method for detecting disconnection of an extracorporeal blood-based therapeutic device by comparison of the endogenous electrical signals detected at sensors incorporated into (or attached to) tubing carrying blood leaving and returning to a patient, in which similarity of the signals is indicative of safe connection and dissimilarity is indicative of disconnection, wherein there is automated circuitry so as to monitor the similarity and trigger an alarm condition.

It is a further object to provide a method in which an alarm condition, sensed by use of a patient's endogenous electrical voltages and indicating a patient disconnection to an extracorporeal blood-based therapeutic device, triggers a multitude of safety features including but not limited to: audible and visual alarms (proximate or remote); circuitry that would stop any and all blood pumps; and failsafe circuitry that would trigger external clamping to the blood tubing as a further safeguard to prevent unintended continued blood flow.

It is a further object to provide a method for detecting disconnection of an extracorporeal blood-based therapeutic device by comparison of the endogenous electrical signals detected at sensors incorporated into (or attached to) tubing carrying blood leaving and returning to a patient, by means of measuring impedance between those two sensor locations: safe connection to the patient is indicated by a small electrical impedance between the two points; the common mode signals will be similar; and thus the difference between the two signals is small. An unsafe disconnection is indicated by a large impedance and common mode signals that are very different.

It is a further object to provide a method for detecting disconnection of an extracorporeal blood-based therapeutic device by comparison of the endogenous electrical signals detected at sensors incorporated into (or attached to) tubing carrying blood leaving and returning to a patient, in which similarity of the signals is indicative of safe connection and dissimilarity is indicative of disconnection, wherein electrical conductance within the therapeutic device is minimized by rotating roller peristaltic occlusion blood pumps.

It is a further object to provide a method for detecting disconnection of an extracorporeal blood-based therapeutic device by comparison of the endogenous electrical signals detected at sensors incorporated into (or attached to) tubing carrying blood leaving and returning to a patient, in which detection of a cardiac cycle waveform is indicative of a safe connection, and loss of the waveform is indicative of disconnection.

It is a further object to provide a method for detecting disconnection of an extracorporeal blood-based therapeutic device by comparison of the endogenous electrical signals detected at sensors incorporated into (or attached to) tubing carrying blood leaving and returning to a patient, in which detection of a cardiac cycle waveform is utilized to monitor a patient's heart rate and rhythm.

It is a further object to provide a design for blood tubing for said device so as to incorporate a conductive element added to, or integral to, the tubing so as to conduct a patient's endogenous electrical voltages in a low impedance state.

Other aspects and advantages of the invention will become apparent from the following detailed description taken in conjunction with the accompanying drawings, illustrating, by way of example, the principles of the invention.

BRIEF DESCRIPTION OF THE DRAWINGS

In order that the manner in which the above recited and other advantages and objects of the invention are obtained, a more particular description of the invention briefly described above will be rendered by reference to specific embodiments thereof, which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Figure 1:
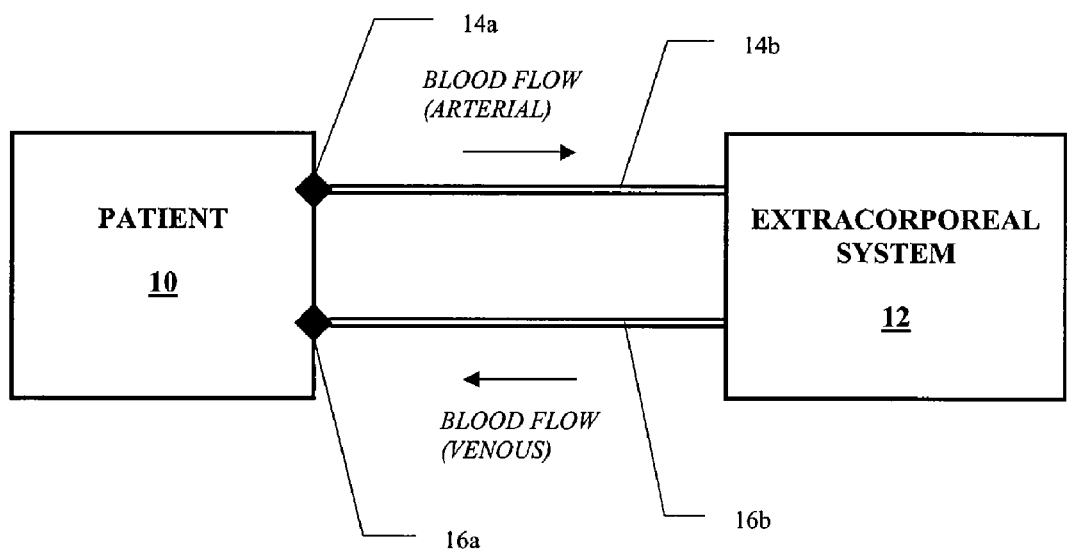
FIG. 1 illustrates a schematic view showing two needles insertable within a patient through which blood flows along a blood path to and from an extracorporeal system of the prior art.

Referring now to the drawings, the preferred embodiment of the present invention will be described. The fluid referenced in the embodiments herein comprises blood and the extracorporeal system includes, for example, a hemodialysis device. However, the invention would also be applicable to other fluids and blood components transmitted via tubing, and other extracorporeal devices, as known in the art.

FIG. 1 illustrates a schematic view showing two needles 14a, 16a insertable within a patient 10 through which blood flows to (first needle/arterial needle 14a) and from (second needle/venous needle 16a) an extracorporeal system 12 of the prior art through first tubing/"arterial" tubing 14b carrying blood away from the patient and second tubing/"venous" tubing 16b carrying blood back to the patient. Significant morbidity or mortality can result from hemorrhage when extracorporeal therapeutic devices incorporating blood pumps are accidentally disconnected from patients. During hemodialysis therapy, for example, blood flows from the patient 10 through the arterial needle 14a to the extracorporeal blood system 12 includes, for example, a hemodialysis machine, via the tube member 14b where the blood is treated and delivered to the patient 10 through the venous needle 16a via the tube member 16b.

To address this clinical need, the present invention provides for a method of passive monitoring that utilizes the patient's endogenous voltages. In the preferred embodiments these electrical signals are transmitted by blood which is naturally electrically conductive.

Specifically, the present invention utilizes passive monitoring of endogenously-occurring electrical voltages (those voltages produced naturally by the patient's body). Endogenous voltages have long been studied and have included those from the heart, brain, nerves and muscle. The resultant medical devices have become part of our everyday diagnostic armamentarium, such as those that produce electrocardiograms and electroencephalograms.

However, designing circuitry to make use of endogenous voltages is particularly difficult in the case of extracorporeal therapeutic devices for three main reasons, all of which are addressed in the present invention: 1) the points from which the blood leaves and returns to the body may be in such close proximity (e.g. 2 cm) that the endogenous electrical signals could be nearly identical; 2) the electrical continuity of the extracorporeal path within the therapeutic medical device could cause an effective shunt attenuating or eliminating signals to or from the patient that would have been used to discriminate a disconnection status; and 3) the current standard technique for blood pumping is that of rotating occlusion (peristaltic) spring-loaded roller pumps, which periodically occlude the tubing segments, displacing the conductive blood and thereby alter the electrical conductivity. Each of these issues is overcome by the present invention and are all addressed below.

Nearly all extracorporeal therapies are characterized by the blood leaving the body from a site in close proximity to where the processed blood returns. For example, the blood may exit the body via a needle 2 to 3 cm from the second needle, which returns the processed blood. Endogenous electrical voltages monitored at locations of such close proximity are of necessity extremely similar. They reflect a variety of local and distant electrical signals, including those from the heart and nearby muscles.

Figure 2:
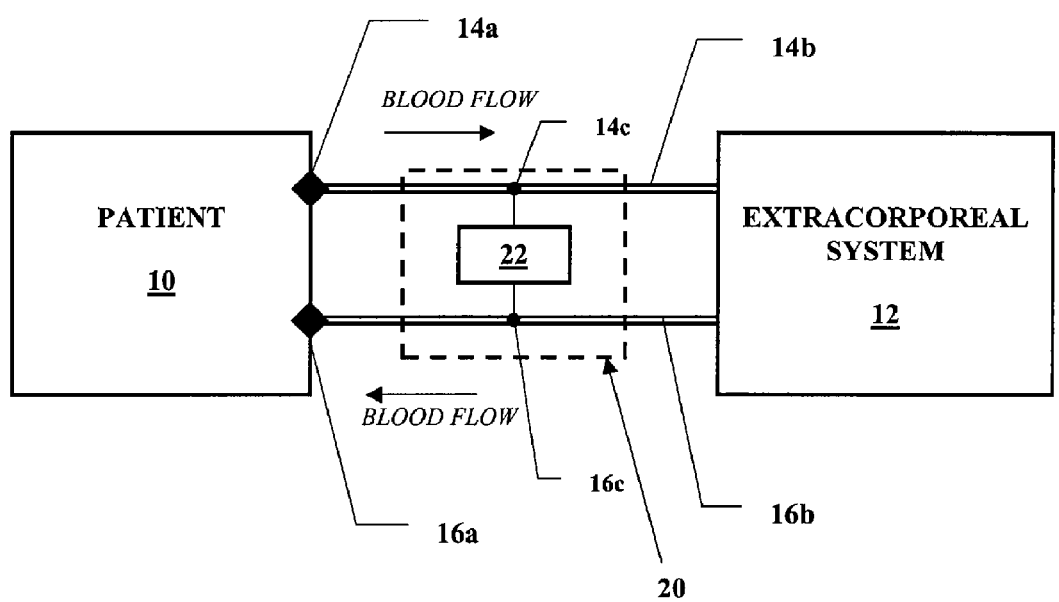
FIG. 2 illustrates a schematic view of an embodiment of the present invention connected to the blood path capable of detecting needle dislodgment.

Turning now to FIG. 2, the present invention provides medical devices, apparatuses, systems, and methods that employ, in part, apparatus 20 comprising circuitry 22 and contact points 14c, 16c in fluid contact and/or electrical communication with a fluid circuit allowing a direct conductivity measurement to be used such that dislodgment of a needle or other access device through which fluid flows between a patient and the fluid circuit can be immediately detected. Specifically, the present invention uses circuitry 22 capable of comparing the signals at contact points 14c, 16c in two tubing segments 14b, 16b (or other analogous sites in the extracorporeal apparatus), one containing blood leaving the patient (arterial 14c) and the other returning blood to the patient (venous 16c). In the invention's simplest embodiment, when all connections are safe, subtracting the nearly identical signals at the two tubing segments yields a resultant value of nearly zero.

Figure 3:
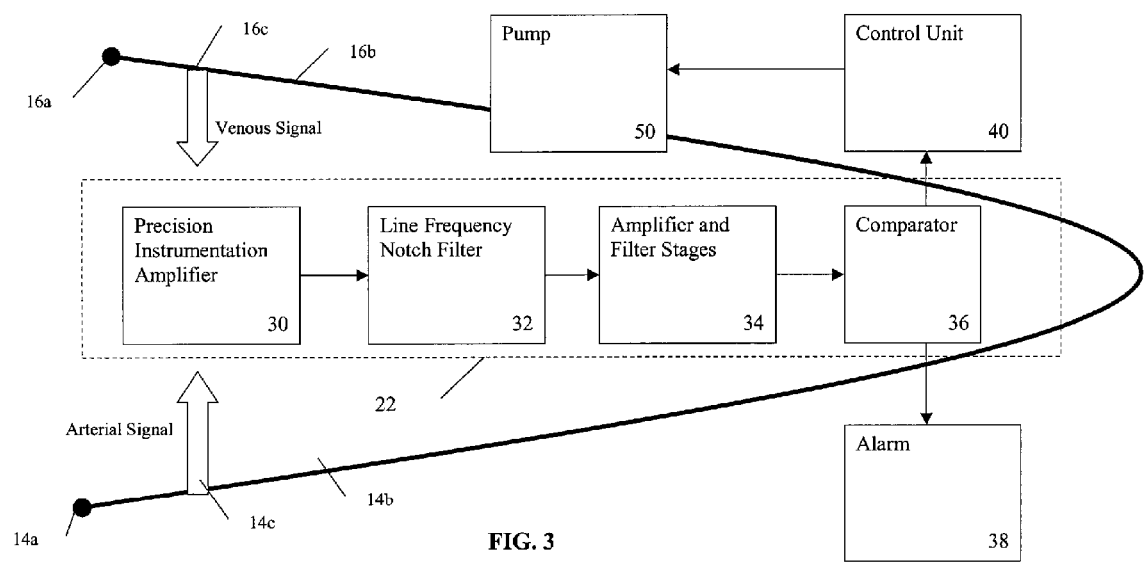
FIG. 3 illustrates a sample block diagram of example components that may be used in an embodiment of the present invention.

Turning now to FIG. 3, a simple block diagram illustrating sample components that may be used to implement the present invention is shown. The circuitry 22 (collectively referenced for illustrative purposes only by broken lines, wherein the lines do not breach the blood tubing) preferably comprises precision instrumentation amplifier 30, line frequency notch filter 32, amplifier and filter stages 34, and a comparator 36. The invention further comprises an alarm 38. A simple threshold circuit may be incorporated so that the variance from exactly zero does not trigger false alarms. Control Unit 40 may also be provided to control the pump 50 or other devices.

Disconnection of a blood tubing segment or needle from the patient causes a huge change in that particular signal, when sensed downstream from the disconnection. Thus the difference between the signals sensed at contact points 14c, 16c in the two tubing segments 14b, 16b would no longer be null, and would trigger the alarm condition.

An alarm state would incorporate various safety features to protect the patient from harm. These safety embodiments would include, but not be limited to: audible and visual alarms (e.g., Alarm 38); circuitry (e.g., Control Unit 40) that would stop any and all blood pumps; and failsafe circuitry (e.g., Control Unit 40) that would trigger external clamping to the blood tubing as a further safeguard to prevent unintended continued blood flow.

In the simplest preferred embodiment the presence of connection or disconnection is therefore determined by examining the difference between endogenous voltages at two points 14c, 16c in the extracorporeal blood tubing pathway 14b, 16b. In use, appropriate voltages and impedances are measured at various points within the extracorporeal fluid (e.g., blood) path, and the electrical waveforms are monitored. The electrical voltages and associated waveforms are conducted by the column of blood.

Figure 4:
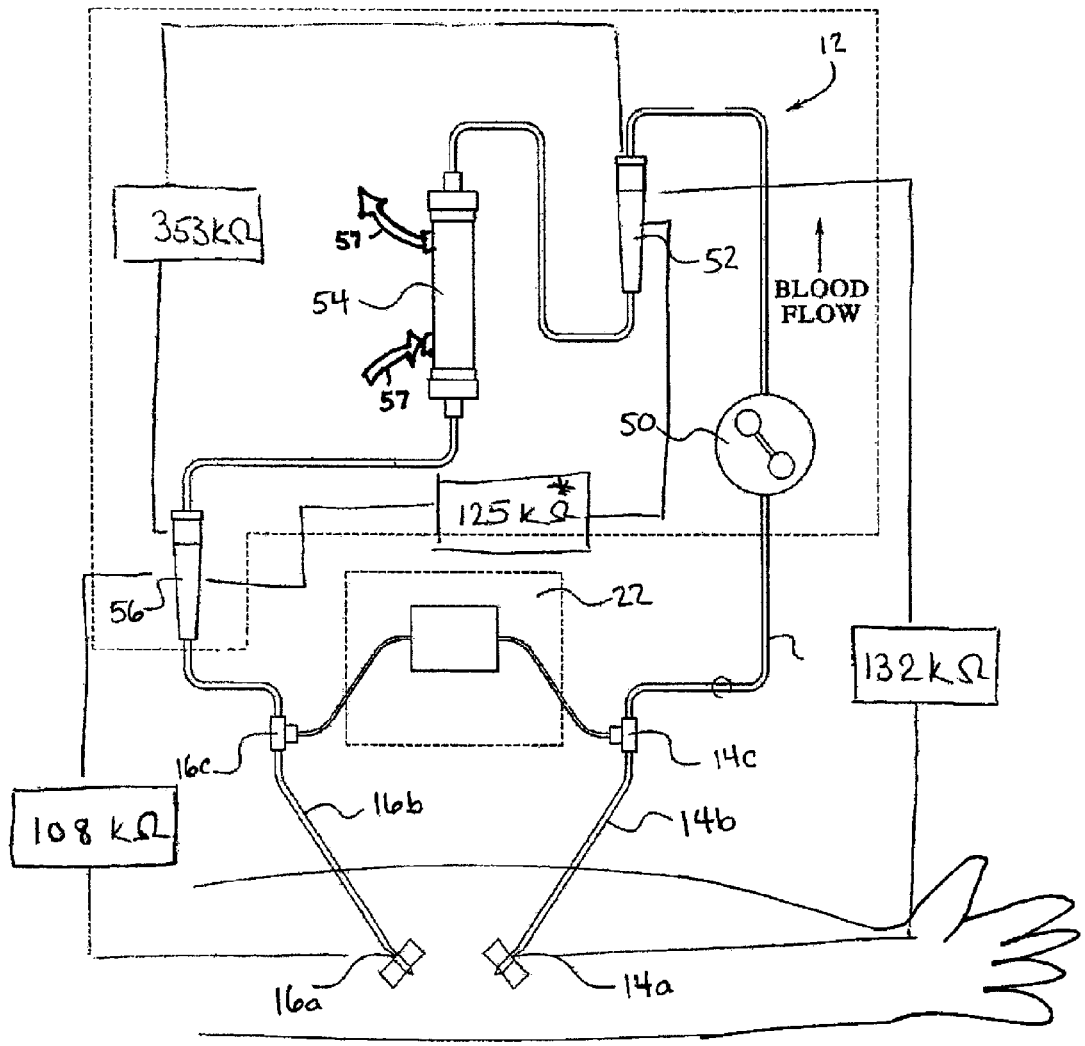
FIG. 4 illustrates a schematic view of an embodiment of the present invention capable of detecting needle dislodgment during hemodialysis therapy.

Specifically, FIG. 4 illustrates a schematic view of an embodiment of the present invention capable of detecting needle dislodgment during hemodialysis therapy showing the arterial limb 14b of the extracorporeal tubing with 132K ohms impedance from the arterial vascular access site 14a to the arterial drip chamber 52. Also shown is the venous limb 16b of the extracorporeal tubing with 108K ohms impedance from the venous drip chamber 56 to the venous vascular access site 16a. The 125K ohms resistance is measured between venous drip chamber 56 and arterial drip chamber 52 when 16a and 14a are correctly in place with pump 50 removed. The extracorporeal system 12 is shown herein with a hemodialyzer 54. In this example, the set of measurements between the arterial drip chamber 52 and the venous test point are set forth in Table 1.

TABLE 1

Distance and Impedance Measurements of Circuit for Hemodialysis Embodiment

| | Distance | Impedance |
|---|---|---|
| Through needles | 113.3" | 156 Kohms |
| Through dialyzer | 149.5" | 436.9 Kohms |

Where the two points of vascular access (e.g. hemodialysis access needles) are close together, or where there is a small (<300 kΩ) electrical impedance between the two points, common mode signals will be similar and thus the difference between the two signals is small. If impedance is large and common mode signals are very different, the difference signal is large (the instrumentation amplifier may even become unstable and begin to oscillate).

Figure 5:
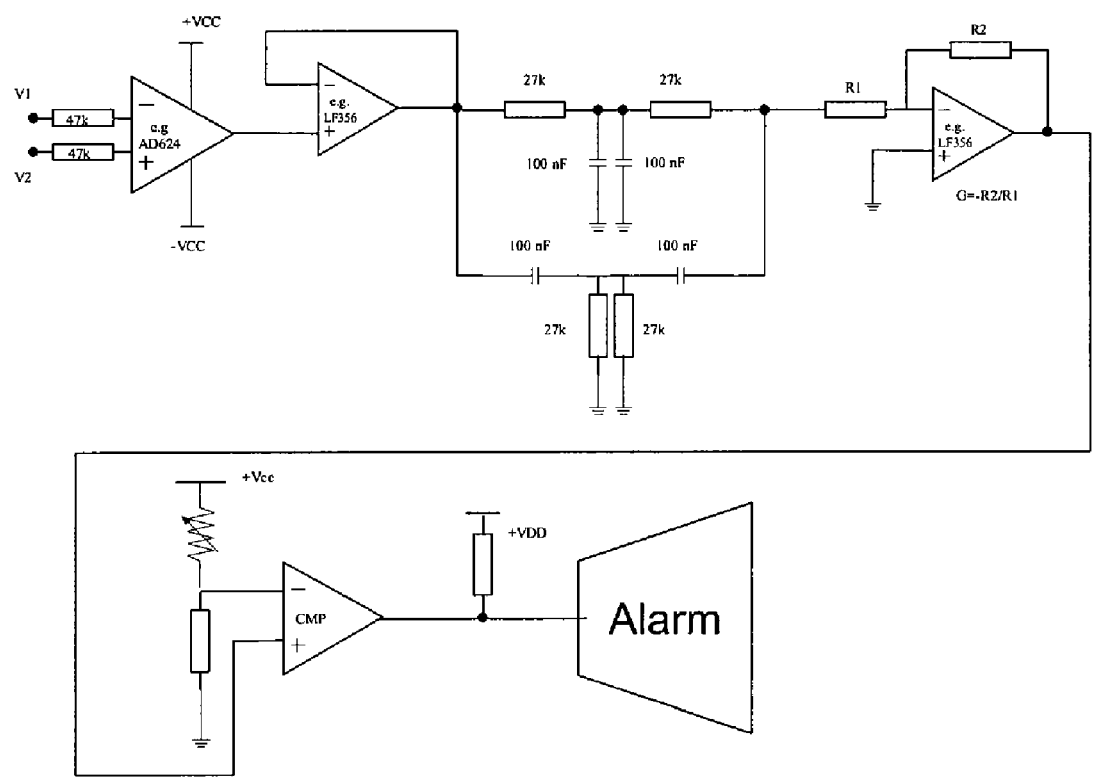
FIG. 5 illustrates an exploded view of an example electrical circuit in an embodiment of the present invention.

Turning now to FIG. 5, a sample circuit diagram is shown that may be used to implement the present invention.

Since so little resistance is caused by the blood in the tubing (up to a few meters in length), the electrical signals can be monitored relatively remote from the patient. The signal waveforms and magnitudes are very similar whether sensed using metal needles inserted through the skin or using electrodes within the blood tubing meters away (see Table I, indicating sensor placement at various locations in the tubing flow path). Thus the sensing electrodes can easily be positioned at the medical therapeutic device meters away from the patient, and they can effectively detect the disconnection. Moreover, the venous electrode could be placed in the dialysate fluid in the dialysate effluent pathway (partially illustrated by reference numeral 57 in FIG. 4). In an embodiment, the electrode can be built into the hemodialysis machine, preferably at a non-sterile part of the pathway, to further save expense of a conductively modified electrode in the venous blood tubing. In that manner, only the disposable arterial tubing would have the conductive element.

The invention includes different methods of transmitting the endogenous electrical signals to the sensor circuitry. The blood itself is an adequate conductor of the signal to the apparatus a few meters away. At that remote location the signal is conducted from the inner lumen containing the blood to the outer surface of the tubing (and henceforth to the electrode contact) utilizing a variety of possible embodiments.

In a preferred embodiment, electrical continuity between a sensor electrode external to the tubing and the conductive blood inside the tubing can be accomplished by making the tubing wall electrically conductive at the point of attachment. This can be effected by using sterile biocompatible electrodes fabricated so as to traverse the wall of the blood tubing.

Various types of conductive elements spanning the tubing wall would accomplish this goal, and could include metallic or nonmetallic (e.g. carbon black) structures.

In one embodiment of the invention designed for a hemodialysis machine, for example, conductive electrodes located on the hemodialysis machine would be attached to appropriate conductive sites on the outer surface of the arterial and venous tubing or drip chambers.

In an alternative but related strategy, the entire length (or shorter segments) of the tubing (e.g. one located in the tubing leaving the patient, one in the tubing returning to the patient) can be fabricated so as to be electrically conductive. Thus, the electrical signal would be transmitted via the tubing itself, and not necessarily rely on the blood for conductance. In instances wherein metallic needles are used to gain access to the vasculature, the signal would thus be conducted from the body via the metallic needle to the conductive tubing and henceforth to the electrical sensor, remote from the patient. For example, the tubing could be co-extruded with a biocompatible conductive substance, such as carbon black, or manufactured with a conductive metallic wire or thread.

Importantly, a benefit of using a conductive element integral to the tubing is that the conductor can be chosen to have an impedance less than that of blood, which is a scenario described in more detail below.

Another embodiment includes transmitting the endogenous electrical signal from the patient to the remote sensor apparatus via a separate low impedance conductive element (such as a wire), entirely distinct from the blood tubing.

The circuit of the invention can be designed in its simplest embodiment for those therapeutic devices in which there is not a continuous blood path through the extracorporeal device and thence to the tubing returning to the patient. Under those circumstances, there is in effect no electrical shunt through the medical device itself. Accidental tubing or device disconnection thus causes huge differences in the electrical signals from the two sensors, and easily triggers an alarm condition (Table I, example wherein sensors are placed at arterial and venous needles). This is somewhat similar to current extracorporeal therapies that use roller occlusion peristaltic rotating pumps. By virtue of the spinning spring-loaded rollers which occlude segments of the tubing, there is near-discontinuity of the column of blood in the tubing. There is only minimal electrical continuity through the occluded segment within the pump (Table I, example wherein there is pump tubing occlusion, with or without the pump spinning). Furthermore, depending on the pump design there may periodically be more than one occluded segment as more than one roller presses against the tubing. The periodicity of the intermittently extremely high electrical resistance through those occluded segments eliminates the potential shunt phenomenon that would have dampened the alarm circuit's sensitivity. With pump operation, the characteristic impedance between measurement points will vary, since the pump periodically completely occludes tubing and therefore increases the impedance through the dialyzer part of the blood tubing pathway.

Since the invention can be incorporated into a therapeutic device with said roller pump, it will be possible to lock the disconnection detection circuit to the pump frequency. In this embodiment, since disconnection is easier to establish when the electrical path within the therapeutic device is interrupted, disconnect detection would only performed at those times.

Other embodiments of the invention function for extracorporeal devices that are characterized by continuous electrically conductive blood flow paths between the tubing leaving the patient and that which returned to the patient (e.g. electrical continuity within the therapeutic device, and without high impedances caused by occlusion pumps, as in Table I). The alarm circuit is able to detect a disconnect status as long as the impedance of that shunting pathway within the device is significantly higher than the typically low value between the sensors and the patient. The latter impedance can be further minimized by a variety of methodologies: the sensor electrode can be positioned closer to the patient or improved electrical conduction can be accomplished by a metallic wire or conductive stripe (with lower impedance than blood) fabricated into the tubing (described above).

Another embodiment of the invention pertains to extracorporeal devices or blood access scenarios in which the sites of blood egress and re-entry to the body are not in close proximity. An example would be blood exiting the body from one extremity and returning to a needle in a different extremity. Another example would be one vascular access site in an extremity and another at a central vein. In these circumstances the alarm circuitry would detect electrical differences between the sensors analogous to an electrocardiogram signal. Although the waveform would be very different from a standard electrocardiogram for routine clinical use, the invention would succeed in detecting each cardiac cycle. Loss of the cardiac signal would trigger the alarm state. The periodicity of the electrical signal could also be used to monitor the heart rate and cardiac rhythm, which would be of clinical benefit for monitoring the patient during the extracorporeal treatment.

Although preferred illustrative embodiments of the present invention are described above, it will be evident to one skilled in the art that various changes and modifications may be made without departing from the invention. It is intended that the appended claims cover all such changes and modifications that fall within the true spirit and scope of the invention.

What is claimed is:

1. A method of detecting the disconnection of an extracorporeal device, wherein blood from proximate vascular access points of a patient travels through an extracorporeal blood path comprising an arterial line in fluid communication with a first vascular access point, a blood treatment device, and a venous line in fluid communication with a second vascular access point, comprising:
   (a) removing blood from a patient, passing it through the extracorporeal device, and returning it to the patient;
   (b) obtaining a value representative of endogenous electrical signals of a patient along the extracorporeal blood path;
   (c) comparing the obtained value to a predetermined threshold value; and
   (d) triggering a safety response in the extracorporeal blood path when the obtained value substantially meets or exceeds the threshold value, thereby indicating disconnection.

2. The method of claim 1 wherein the value is obtained by measuring the difference between endogenous voltages at two points along the blood path.

3. The method of claim 1 wherein the value is obtained by measuring impedance between two points along the blood path.

4. The method of claim 1, wherein sensors are placed remote from the patient to obtain the value, such that a first sensor is in communication with blood in the arterial line and a second sensor is in communication with blood in the venous line.

5. The method of claim 1, wherein sensors are placed to obtain the value, such that a first sensor is in communication with an arterial access needle and a second sensor is in communication with a venous access needle.

6. The method of claim 1, wherein sensors are placed to obtain the value, such that a first sensor is in communication with an arterial drip chamber and a second sensor is in communication with a venous injection port to obtain the value.

7. The method of claim 1, wherein sensors are placed to obtain the value, such that a first sensor is in communication with an arterial drip chamber and a second sensor is in communication with a venous drip chamber to obtain the value.

8. The method of claim 1 wherein the blood path comprises tubing that is electrically conductive at the point of attachment of one or more sensors placed to obtain the value.

9. The method of claim 1 wherein the blood path comprises tubing that is electrically conductive along part of its length.

10. The method of claim 1 wherein the blood path comprises tubing that is electrically conductive along its entire length.

11. The method of claim 1 wherein the blood path comprises tubing having an electrically conductive element along its entire length.

12. The method of claim 1 further comprising a separate conductive element connected between the vascular access and a remote sensor used to obtain the value.

13. The method of claim 1 further comprising indicating a safe connection when the obtained value does not exceed the threshold value.

14. The method of claim 1, wherein the safety response comprises an alarm selected from the group consisting of visual and audible alarms.

15. The method of claim 1, wherein the safety response comprises closing a cutoff clamp in the venous line.

16. The method of claim 1, wherein the safety response comprises interrupting the provision of blood to the extracorporeal blood path.

17. The method of claim 1, wherein the safety response comprises stopping a blood pump provided in the arterial line.

18. The method of claim 1 wherein the step of obtaining a value based on endogenous electrical signals of a patient along the extracorporeal blood path comprises obtaining the value when the tubing in the blood path is periodically occluded during blood pump operation.

* * * * *